United States Patent [19]

Cheetham

[11] 4,264,354
[45] Apr. 28, 1981

[54] METHOD OF MAKING SPHERICAL DENTAL ALLOY POWDERS

[76] Inventor: Jeffery J. Cheetham, 5, Brunsdon St., Bayswater, Victoria 3153, Australia

[21] Appl. No.: 62,343

[22] Filed: Jul. 31, 1979

[51] Int. Cl.³ .......................... C22C 7/00; C22C 5/06; B22F 1/02
[52] U.S. Cl. ...................................... 75/0.5 B; 75/251
[58] Field of Search .................... 75/251; 264/15, 16; 75/169, 0.5 B

[56] References Cited

U.S. PATENT DOCUMENTS

| | | | |
|---|---|---|---|
| 2,952,868 | 9/1960 | Rowan | 18/1 |
| 2,969,281 | 1/1961 | Monson | 75/0.5 |
| 3,015,852 | 1/1962 | Hoffman et al. | 18/48 |
| 3,272,615 | 9/1966 | Hoffman et al. | 75/0.5 |
| 3,305,356 | 2/1967 | Youdelis | 75/134 |
| 3,933,961 | 1/1976 | Burns | 264/11 |
| 3,943,211 | 3/1976 | Dickey | 264/15 |
| 3,989,512 | 11/1976 | Sayce | 75/11 |
| 3,997,327 | 12/1976 | Tolliver | 75/0.5 R |
| 3,997,330 | 12/1976 | Aliotta et al. | 75/0.5 R |
| 4,071,588 | 1/1978 | Fey et al. | 264/15 |
| 4,076,640 | 2/1978 | Forgensi et al. | 252/62.1 R |
| 4,162,283 | 7/1979 | Borer et al. | 264/15 |
| 4,164,419 | 8/1979 | Kaji et al. | 75/169 |

*Primary Examiner*—G. Ozaki
*Assistant Examiner*—Upendra Roy
*Attorney, Agent, or Firm*—Larson, Taylor and Hinds

[57] ABSTRACT

A dental alloy powder containing silver, tin and copper and, optionally, other alloying metals which has been rendered spherical by a heat treatment to melt at least a surface stratum of the particles of the alloy, followed by cooling.

11 Claims, No Drawings

METHOD OF MAKING SPHERICAL DENTAL ALLOY POWDERS

The present invention relates to dental alloy powders.

BACKGROUND OF THE INVENTION

Dental amalgam as used in clinical practice for the restoration of decayed teeth, is prepared in the surgery by mixing amalgam alloy with mercury to form a plastic paste, which after being packed into a prepared cavity, hardens to form a sealing restoration to restore the function of the tooth.

The formed amalgam consists essentially of remnants of the original alloy particles held in a matrix of silver-mercury compound (known as the Gamma 1 phase), and tin-mercury compound (known as the Gamma 2 phase). It has been shown that the weakest and most corrodible component in the amalgam is the Gamma 2 phase. Thus, this component of the amalgam should be reduced to a low level but not necessarily eliminated as this may lead to brittleness problems in the amalgam.

Reduction of the Gamma 2 phase can be effected by (a) manipulation of the amalgam by the dentist during condensation of the amalgam, providing suitable access to the cavity is possible, or (b) chemo-metallurgical reactions within the amalgam.

Method (a) suffers from the drawback that suitable access to the cavity it not always possible. Thus, it is desirable for an amalgam alloy to possess properties facilitating operation of method (b).

Work by Dr. D. Mahler of the University of Oregon has shown that it is possible to predict the future behaviour of an amalgam in clinical service by the use of what is known as the Static Creep test.

While the Static Creep test does not measure an absolute property of the material, it nevertheless does measure some physical property which can be correlated to clinical behaviour. In the test, a seven day old specimen of amalgam held at mouth temperature (37° C.) is basically subjected to a Creep test. It seems desirable for an amalgam to demonstrate a low figure for this property, which, although unrelated, seems to be a function of the use of low Gamma 2 content alloys.

In the past, alloys which produced amalgams with low Gamma 2 contents were produced by one of two methods. The first method may be termed additive blending. In this method particles, usually spherical, of silver-copper eutectic are added in approximately 30% amount to a conventional lathe cut alloy. Reduction of Gamma 2 phase is achieved by migration of tin from the Gamma 2 phase to the high copper areas of the eutectic. This method suffers from the disadvantage of atmospheric corrosion of the reactive additive due to the high copper content of the eutectic.

The second method involve producing spherical particles by atomization from molten metal. Again, Gamma 2 reduction is achieved by tin migration to high copper areas. This method suffers from the disadvantage that only one particle type can be produced and also the yield of suitably sized particles for dental purposes is low.

A further desirable feature of dental alloy powders is that the particles be spherical. Method (b) above produces spherical particles but is subject to inherent disadvantages as mentioned.

Also, in order to obtain an alloy powder of appropriate characteristics it is often desirable to admix particles of different compositions.

SUMMARY OF THE INVENTION

The present invention provides an alloy powder which can contain any combination of particle types, has spherical particles of any particular desired size and size distribution, is produced in high yield and produces amalgams of controlled physical properties.

In accordance with the present invention there is provided a dental alloy powder containing silver, tin, copper and, optionally, one or more other alloying metals, wherein solid particles of said dental alloy powder have been rendered spherical by passing them through a heating zone so as to melt at least a surface stratum thereof, and then cooling the particles so as to solidify the melted portion.

DESCRIPTION OF THE PREFERRED EMBODIMENTS

The silver, tin and copper contents of the alloy powders of the present invention are not critical and may vary over wide ranges. Preferably, the alloy powder may contain from 35 to 85%, more preferably, 40 to 75%, silver, from 7.5% to 40%, more preferably from 10 to 30%, tin, and from 5 to 40%, preferably from 10 to 30%, copper. The additional alloying ingredients such as zinc or indium are preferably present in amounts from 0-2%.

It will be appreciated that the alloy powder of the present invention is rendered spherical by a heat treatment in which the particles remain separate from one another. Thus, prior to the heat treatment it is possible to admix particles of different compositional characteristics to obtain a final alloy powder having desired characteristics. The percentage values recited above are thus average values for any particular alloy powder. Also, since the particles remain separate from one another, the desired particle size and size distribution for the final product can be selected prior to the heat treatment.

Preferably, the particles to be heat treated are obtained from an ingot of the metal. The ingot is produced by melting the constituent metals of the alloy in the required weight proportions. The melting may be achieved by high frequency induction. The melt is cast under reducing conditions into an ingot.

The ingot is preferably homogenized by annealing. The homogenized ingot is comminuted by lathe to produce fine turnings.

The lathe cut particles are subjected to size reduction such as by ball milling. Typically, the particles are size reduced to a distribution of 0.5 microns to 100 microns particle size.

For preferred dental practice particles up to 5 microns are removed such as by elutriation, and particles above 40 microns are removed such as by sieving.

The retained particles of size 5 microns to 40 microns are injected into and through a heating zone. This is achieved by entraining the particles in a stream of inert gas such as nitrogen although compressed air can be used if desired. The inert gas is at an elevated pressure such as 40–100 psi, preferably 45–55 psi. The heat treatment is preferably carried out in a closed container containing an atmosphere of an inert gas such as nitrogen.

The heating zone is preferably in the form of a flame produced by the combustion of a gas at elevated pressure. The particles are passed through the reducing section of the flame so as to avoid oxidation thereof. The flame may be produced by combustion of any gas which produces a temperature sufficient to achieve the desired end result. Examples of suitable gases are oxyacetylene, hydrogen and liquid petroleum gas.

The particles are passed through the flame at a rate which is controlled by the carrier gas pressure. The particles may be injected from a nozzle about 5 cms from the flame and may reside in the flame for a period of up to 20 microseconds.

As an alternative to the flame, the particles may be passed through a high frequency induction coil which creates a heat plasma.

The heat treated particles are preferably cooled by immersion in a liquid such as water. The spherical alloy particles are retrieved from the liquid and may be cleaned by treatment with hydrochloric acid. The washed alloy is preferably vacuum dried.

The dried alloy may be stress relief annealed under reducing conditions.

The alloy powder so prepared is totally spherical and may be used on its own or blended with non-reactive conventional lathe cut alloy for manipulative characteristics.

The present invention will now be illustrated by the following example.

EXAMPLE

Silver, tin, copper and indium in approximate weight percentages of 60, 26, 14 and 0.5 respectively, were melted together by high frequency induction, and cast under reducing conditions into an ingot about 50 cm in diameter, and 300 cm in length, weighing approximately 6 kg. The ingot was homogenized by annealing at about 400° C. for three days, quenched under water, and reannealed for three days at 410° C. The homogenized ingot was comminuted by lathe to produce fine turnings.

The lathe cut particles were ball milled for 24 hours to reduce the size of the particles to a size distribution of 0.5 microns to 100 microns. Particles up to 5 microns were removed by elutriation and particles above 40 microns were removed by sieving.

The remaining particles of 5–40 microns were injected into a flame produced by combusting liquid petroleum gas at 40 psi in air. The flame had an approximate temperature of 1500° C. The particles were injected into and through the reducing cone of the flame using a carrier gas of nitrogen at a pressure of 50 psi.

The particles were injected from a nozzle about 5 cms from the flame. The heat treated particles were passed into cooling water held at 5° C.

The cooled, now spherical alloy particles were retrieved from the water and cleaned by treatment with 2 N hydrochloric acid and, then vacuum dried at 60° C., and finally stress relief annealed at 150° C. under reducing conditions. The obtained dental alloy powder was mixed with mercury in the ratio of 10 to 10 parts, using a high energy vibratory mixture vibrating at 4300 cpm. The time of mixing was ten seconds. Specimens of the resultant amalgam were tested according to the methods described in Australian Standard AS2110 and American Dental Association Specification No. 1. The results of such tests were:

| | | |
|---|---|---|
| Compressive strength at | 30 seconds | 20,000 psi |
| Compressive strength at | 1 hour | 32,000 psi |
| Plastic Deformation | | 0.18% |
| Dimensional change at | 24 hours | 1.5 micron/cm |
| Static Creep | | 0.2% |

Modifications and variations such as would be apparent to a skilled addressee are deemed within the scope of the present invention.

I claim:

1. A method of producing a spherical dental alloy powder containing silver, tin, copper and, optionally, one or more other alloying metals, which comprises the following steps:
   (1) forming irregular solid particles of said alloy having a particle size distribution in the range from about 0.5 microns to about 100 microns;
   (2) entraining irregular solid particles from step (1) in a stream of inert carrier gas at elevated pressure so as to separate the particles from one another;
   (3) injecting said stream of inert carrier gas containing said irregular, separated, solid particles into and through a heating zone so as to melt at least a surface stratum of the particles;
   (4) passing the heat treated particles from step (3) into a body of liquid so as to cool the particles by immersion in said body of liquid; and
   (5) retrieving said cooled particles from the body of liquid.

2. A method according to claim 1, wherein said stream of inert carrier gas is at a pressure in the range from about 40 to 100 p.s.i.

3. A method according to claim 2, wherein said stream of inert carrier gas is at a pressure in the range from about 45 to 55 p.s.i.

4. A method according to claim 1, wherein said heating zone is in the form of a flame produced by combustion of a gas at elevated pressure, said flame having a reducing cone and said particles being passed through said reducing cone.

5. A method according to claim 1, wherein step (3) is performed in a closed container containing an atmosphere of an inert gas.

6. A method according to claim 5, wherein the inert gas is nitrogen.

7. A method according to claim 1, wherein, subsequent to step (1) and prior to step (2), the irregular particles are subjected to size selection procedures to retain particles having a particle size distribution in the range from about 5 microns to about 40 microns.

8. A method according to claim 1, wherein said body of liquid in step (4) is water.

9. A method according to claim 1, wherein said alloy powder contains from about 35 to 85% silver, from about 7.5 to 40% tin, from about 5 to 40% copper and from 0 to 2% indium.

10. A method according to claim 9, wherein said alloy powder contains from about 40 to 75% silver, from about 10 to 30% tin, from about 10 to 30% copper and from about 0 to 2% indium.

11. A method according to claim 1, wherein said irregular particles of step (1) are obtained from an ingot of the alloy by comminution thereof to produce fine turnings and then subjecting the fine turnings to size reduction.

* * * * *